(12) United States Patent
Rosocha et al.

(10) Patent No.: US 9,932,283 B2
(45) Date of Patent: Apr. 3, 2018

(54) CROSS COUPLING OF 2-BROMO-1-PHENYL INDENES WITH PHENYL ACETYLENES AND OTHER SUBSTITUTED ACETYLENES IN WATER

(71) Applicant: Gregory Rosocha, Toronto (CA)

(72) Inventors: Gregory Rosocha, Toronto (CA); Robert Batey, Toronto (CA)

(73) Assignee: Gregory Rosocha, Toronto (CA)

( * ) Notice: Subject to any disclaimer, the term of this patent is extended or adjusted under 35 U.S.C. 154(b) by 0 days.

(21) Appl. No.: 14/437,646

(22) PCT Filed: Oct. 24, 2012

(86) PCT No.: PCT/IB2012/002075
§ 371 (c)(1),
(2) Date: Apr. 22, 2015

(87) PCT Pub. No.: WO2014/064478
PCT Pub. Date: May 1, 2014

(65) Prior Publication Data
US 2015/0291492 A1 Oct. 15, 2015

(51) Int. Cl.
| | | |
|---|---|---|
| C07C 29/32 | (2006.01) |
| C07C 1/00 | (2006.01) |
| B01J 19/00 | (2006.01) |
| C07D 217/04 | (2006.01) |
| C07D 303/48 | (2006.01) |
| C07D 471/06 | (2006.01) |
| C07C 2/86 | (2006.01) |
| C07C 201/12 | (2006.01) |
| C07C 253/30 | (2006.01) |
| C07C 17/23 | (2006.01) |
| C07C 23/18 | (2006.01) |
| C07C 25/22 | (2006.01) |

(52) U.S. Cl.
CPC ............ *C07C 29/32* (2013.01); *B01J 19/0093* (2013.01); *C07C 1/00* (2013.01); *C07C 2/861* (2013.01); *C07C 17/23* (2013.01); *C07C 23/18* (2013.01); *C07C 25/22* (2013.01); *C07C 201/12* (2013.01); *C07C 253/30* (2013.01); *C07D 217/04* (2013.01); *C07D 303/48* (2013.01); *C07D 471/06* (2013.01); *B01J 2219/0095* (2013.01); *B01J 2219/00873* (2013.01); *B01J 2219/00984* (2013.01); *C07C 2602/08* (2017.05)

(58) Field of Classification Search
None
See application file for complete search history.

(56) References Cited

FOREIGN PATENT DOCUMENTS

WO    WO 2008037604 A1 *  4/2008    ............. A61K 47/32

OTHER PUBLICATIONS

Cappelli et al., Macromolecules (2007), 40(9), pp. 3005-3014.*
Rosocha, Development and Investigation of Electrocyclization Reactions Leading Towards Indene and Thiatriazole Formation and their Functionalization, Thesis, U. of Toronto, issued Jan. 19, 2012.*
CIPO Examination Report dated Nov. 22, 2017.

* cited by examiner

*Primary Examiner* — Brian J Davis
(74) *Attorney, Agent, or Firm* — Chumak & Company LLP

(57) ABSTRACT

The cross-coupling reaction of 2-bromo-1-phenyl indenes with phenyl acetylenes or propargyl alcohol is disclosed. The cross-coupling reaction uses a palladium catalyst with triphenylphosphine in the absence of a copper co-catalyst. The reaction is carried out with pyrrolidine as the base in water at 120° C.

16 Claims, 7 Drawing Sheets

3-phenyl-2-(phenylethynyl)-1H-indene

3

Chemical Formula: $C_{23}H_{16}$
Exact Mass: 292.13
Molecular Weight: 292.37

3-(3-phenyl-1H-inden-2-yl)prop-2-yn-1-ol

4

Chemical Formula: $C_{18}H_{14}O$
Exact Mass: 246.10
Molecular Weight: 246.30

CROSS COUPLING OF 2-BROMO-1-PHENYL INDENES WITH PHENYL ACETYLENES AND OTHER SUBSTITUTED ACETYLENES IN WATER

FIELD OF INVENTION

The field of the invention relates to a process to make alkyne substituted indene compounds using safer and more economical approaches that involve the use of batch methods and micro flow reactors.

BACKGROUND OF INVENTION

The cross coupling of 2-bromo-1-phenyl indenes with phenyl acetylenes and other substituted acetylenes in water is a very useful process for making new chemical products that have indene and alkyne groups. Acetylenes, alkynes, and propargyl alcohols are important chemicals isolated from petroleum and other natural sources such as biomass and are used for different applications by the pharmaceutical, chemical, oil and gas industry. They are found naturally in oil deposits, in biomass in varying amounts, they are available from major chemical suppliers and inexpensive. Alkynes are reactive chemicals and storage can be problematic which is why they are usually not stored on site for deep sea oil and gas applications during production due to safety concerns from flammability, explosion and lack of space for safe storage of gaseous forms. Further, the reactivity that alkyne gases, liquids and solids have can make them challenging and sometimes difficult to store for extended periods of time due to decomposition. This high chemical reactivity and the different properties of alkynes make them valuable chemicals that are used by chemical and pharmaceutical industries. They have desirable properties that allow them to be used as cross linkers and plasticizers by the plastics industry and as chemical building blocks and intermediates to make medicaments for the pharmaceutical industry. The alkyne structure is found in several pharmaceutical medicaments and continues to be an important chemical that is used and further explored for the properties that they can provide.

Indenes are petroleum products found in the low boiling fractions of heavy oil, coal tar, and bitumen. They have many different applications for different industries. They are used as high energy fuels for marine and land applications, and are found as chemical components in resins, plastics, and performance chemicals. They are also used as valuable intermediates and building blocks for the pharmaceutical industry and have been used for the preparation of medicaments. Indenes are very inexpensive providing a very economical chemical feedstock to make other high value chemicals used by many industries. The availability and low cost of indenes makes them exceptional starting chemicals for different chemical processes.

The process of the present invention provides a way to couple alkynes and indenes. Currently, not a process exists that can couple a methyl or phenyl substituted indene with acetylenes. Methyl indenes do not have a high reactivity when compared to alkenes or aromatics and therefore a process that can couple indenes would be very beneficial. The process described uses available commodity chemicals to make higher value chemicals in water. In addition, additives are not needed which can lead to increased costs and environmental concerns. The process can also be catalytic and can reduce material costs, process costs and manufacturing costs.

Further, the process of the present invention is very versatile and can be performed in batch or in a micro flow reactor providing added advantages. Some processes are difficult to use in micro flow reactors because of compatibility problems associated with the chemicals used in the process. Micro flow reactors have many benefits from safety, control, speed of optimization of reactions and provide higher efficiency. These benefits provide the users of micro flow reactors additional advantages over batch methods due to increased control over these reaction parameters. This added control lowers waste generation and increases chemical yields.

SUMMARY OF INVENTION

This invention is a chemical process for the synthesis of different alkyne and acetylene derived cross-coupled products with excellent yields and efficiencies (20-80% yield) from the reaction between 2-bromo-1-phenyl substituted indenes with phenyl acetylene or propargyl alcohol and can work with other alkynes. The reaction takes place in water in the presence of a palladium salt blend that can contain triphenyl phosphine and can use pyrrolidine and/or piperidine as base in a solvent blend with water at 120° C. without the need for additives such as micellar forming chemicals or copper.

The process in the present invention can make indene coupled alkyne molecules of the structure I and II (claim 1, Drawing 1). Alkynes and propargyl substituted chemicals such as propargyl alcohols can be used in this process to form alkyne and propargyl containing 2-substituted indenes (Drawing 1, and Drawing 2).

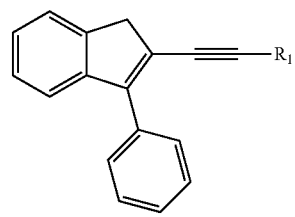

I

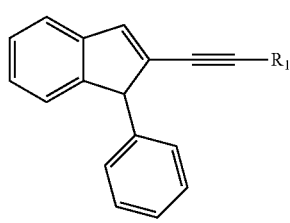

II

Wherein,
$R^1$ can be
  H
  $CH_3$
  $CH_{(n)}CH_3$ (n=1-20)
  $CH_2OH$
  $C_6H_5$
  $C_6H_4R^2$
  a chemical group containing at least one alkyne
  a chemical group containing at least one alkene
  a chemical group that can be considered an alkane
  a chemical group that contains an alkane
  a chemical group that contains a naphthalene ring a chemical group that contains an anthracene ring structure a chemical group that contains a cyclopentadiene ring structure $R^2$=o-$NO_2$, or m-$NO_2$, or p-$NO_2$, o-X, or m-X, or p-X (where X=F, Cl, Br, I)

o-$CF_3$, or m-$CF_3$, or p-$CF_3$ o-OMe, or m-OMe, or p-OMe o-$NH_2$, or m-$NH_2$, or p-$NH_2$ o-OH, or m-OH, or p-OH

The process can be performed in batch or with the use of a flow reactor and microreactor to achieve a continuous manufacturing stream of the high value alkyne and propargyl containing products that can be made using the process of the present invention. Microreactors and flow reactors have been used in chemical manufacturing because of the many advantages they can offer. They are chemical reactors that provide an increase in efficiency, lower costs, provide time savings, and offer an increase in safety associated with their operation in chemical and pharmaceutical discovery and manufacturing when compared to batch methods. The operation can be controlled by a computer interface that allows for quick optimization which minimizes the time associated with research and development of new chemicals and medicaments. The present invention discloses a micro flow reactor for the process to provide an increase in efficiency. This efficiency is obtained from increases in safety, process cost reductions, process time reductions, and less waste being made. These advantages can provide an increase in process efficiency when compared to the batch method. The micro flow reactor design is disclosed in (Drawing 3).

For example, the process can successfully manufacture 3-Phenyl-2-(phenylalkynyl)-1H-indene using 2-Bromo-1-phenyl indene (100.0 mg, 0.370 mmol), phenyl acetylene (80.0 μL, 0.740 mmol), the palladium salt blend that contains at least triphenylphosphine (19.4 mg, 20 mmol %), and palladium chloride (6.40 mg, 10 mmol %), pre-stirred in a round bottom flask for 15-35 minutes, followed by the addition of the solvent blend that contains water (3.70 mL, 0.10 M) and pyrrolidine. Pyrrolidine (61.0 μL, 0.7406 mmol) was added dropwise into the solvent blend forming a light brown mixture. The mixture was heated to 120° C. and monitored using $^1H$ NMR for the formation of the cross-coupled product. Water (20.0 mL) and ethyl acetate (75 mL) was added. The mixture was washed with 1M HCl (3×25 mL), water (3×75 mL) and brine (3×50 mL). The organic phase was dried with sodium sulfate, filtered, and evaporated in vacuo. The remaining residue was purified using silica gel chromatography (0-5% ethylacetate in hexanes) to afford a light yellow oil (86.0 mg, 80% yield). IR (Thin Film): 3047, 3019, 2930, 2347, 2190, 1967, 1599, 1487, 1459, 1443, 1387, 1361, 1333, 1177, 1154, 1126, 1065, 1020, 942, 903, 754, 690 cm-1. $^1H$ NMR (400 MHz, $CDCl_3$) δ 7.79 (2H, dt, J=7.0, 1.5 Hz), 7.56-7.47 (4H, m), 7.46-7.38 (3H, m), 7.34-7.26 (5H, m), 3.76 (2H, s) ppm. $^{13}C$ NMR (300 MHz, $CDCl_3$) δ 148.6, 144.0, 143.2, 134.7, 131.6, 129.0, 128.5, 128.5, 128.3, 128.2, 126.8, 126.2, 124.0, 123.7, 122.8, 121.2, 95.8, 87.5, 42.6 ppm. LRMS (EI+): m/z=293 (8), 292 (100), 291 (46), 289 (26), 276 (4), 215 (14), 144 (3), 131 (1). HRMS (EI+): $C_{23}H_{16}$ calc mass=292.1252. Found=292.1251.

Similarly, in another example, the synthesis of 3-(3-Phenyl-1H-inden-2-yl)prop-2-yn-1-ol can be prepared by pre-stirring a solution of 2-bromo-1-phenyl indene (100.0 mg, 0.369 mmol), propargyl alcohol (25.7 μL, 0.4428 mmol), the palladium salt blend containing at least triphenylphosphine (9.67 mg, 0.036 mmol), and palladium chloride (3.50 mg, 0.020 mmol), stirring for 15-30 minutes followed by the addition of the solvent blend containing piperidine (0.738 mmol, 2.00 equiv.) dissolved in acetone (3.80 mL, 0.10 M) and stirred at room temperature for 10 min. Water (3.0 mL, 0.97 M) was added dropwise. The mixture was heated to 60° C. until the presence of starting material was not detected as determined by TLC analysis. Upon completion, the reaction was quenched with water (3.0 mL), and extracted with diethylether (3×25 mL). The organic phase was dried with sodium sulfate, filtered, and evaporated in vacuo. The remaining residue was purified using silica gel chromatography (10-20% ethylacetate in hexanes) to afford the product as a light orange oil (27.0 mg, 30% yield). IR (Thin Film): 3053, 2914, 2837, 1592, 1488, 1435, 1387, 1323, 1173, 1064, 1036, 920, 881, 851, 782, 699, 658, 614 $cm^{-1}$. $^1H$ NMR (400 MHz, $CDCl_3$) δ 7.78 (1H, s), 7.50-7.40 (1H, m) 7.64-7.52 (6H, m), 7.35-7.30 (4H, m), 2.60 (3H, s) ppm. $^{13}C$ NMR (300 MHz, $CDCl_3$) δ 138.6, 138.0, 134.3, 132.6, 132.5, 132.2, 130.4, 128.7, 128.6, 127.8, 127.3, 126.5, 126.1, 126.0, 21.6 ppm. LRMS (EI+): m/z=47 (5), 49 (24), 77 (3), 84 (53), 86 (33), 94 (4), 128 (2), 139 (2), 187 (4), 189 (8), 202 (53), 215, (39), 237 (4), 251 (7), 252 (100). HRMS (EI+): $C_{18}H_{14}O$ calc. mass=246.1045. Found=246.1042.

In another example, the micro flow reactor disclosed (Drawing 3) can generate 2-alkynyl-1-phenyl indenes by filling the chemical reservoir containers with the corresponding indene and alkynes and triphenylphosphine (1:1: 0.1 molar ratio), base container with pyrrolidine (2.0 molar ratio) and water storage container. The water flow rate is adjusted to 5.0 mL/minute with a Gilson pump to achieve an indene molar concentration of 0.5M. The indene/alkyne flow rate is adjusted to 4.0 mL/min and the pyrrolidine flow rate to 4.0 mL/min. The resultant 3 reaction stream blend is pumped at a rate of 5.0 mL/min through an inline filter, a mixing module for blending the reactant stream and a backpressure regulator to ensure a flow pressure of 30 psi. The reactant flow passes into a glass microreactor unit or flow coil disk coated with palladium bearing a total volume of at least 5 mL-10 mL and channels and grooves of <200 μm or >200 μm that is enclosed within the temperature regulating enclosure and the temperature set to 120° C. When the reaction is complete, the product stream passes through the base scavenging column to remove excess pyrrolidine and through a detector such as an infrared detector (IR), mass spectrometer (MS) or nuclear magnetic resonance spectrometer (NMR). If the desired conversion is not obtained, the reaction stream continues to circulate within the microreactor reaction loop until the reaction is complete. 2-alkynyl-1-phenyl indenes are collected in the chemical product collection chamber. IR (Thin Film): 3047, 3019, 2930, 2347, 2190, 1967, 1599, 1487, 1459, 1443, 1387, 1361, 1333, 1177, 1154, 1126, 1065, 1020, 942, 903, 754, 690 cm-1. $^1H$ NMR (400 MHz, $CDCl_3$) δ 7.79 (2H, dt, J=7.0, 1.5 Hz), 7.56-7.47 (4H, m), 7.46-7.38 (3H, m), 7.34-7.26 (5H, m), 3.76 (2H, s) ppm. $^{13}C$ NMR (300 MHz, $CDCl_3$) δ 148.6, 144.0, 143.2, 134.7, 131.6, 129.0, 128.5, 128.5, 128.3, 128.2, 126.8, 126.2, 124.0, 123.7, 122.8, 121.2, 95.8, 87.5, 42.6 ppm. LRMS (EI+): m/z=293 (8), 292 (100), 291 (46), 289 (26), 276 (4), 215 (14), 144 (3), 131 (1). HRMS (EI+): $C_{23}H_{16}$ calc mass=292.1252. Found=292.1251.

DETAILED DESCRIPTION OF THE EMBODIMENTS OF THE INVENTION

In one embodiment of the present invention, the process can use water which is the safest solvent that is available to use for industrial processes because of safety considerations. Water is not flammable and does not pose concerns that can be problematic for industrial processes. It is easy to handle by personnel and does not have short term or long term health effects. In addition water is available in every industrial area that produces chemicals from petroleum or coal tar chemical feedstocks providing a process that can be used by different regions of the world with different economic capabilities.

In another embodiment of the present invention, the process can use two different solvents. Water can be used in addition to water containing a base which provides a solvent that is different and has other physical properties when compared to only water. Water is a solvent which is a very safe solvent to use because there are no flammability concerns. In addition, water is safer than other solvents that are used in cross coupling reactions since most cross coupling reactions use an organic solvent that can have industrial restrictions and safety concerns. In addition, base can be used in the solvent blend providing an added advantage since other processes are not tolerant to these changes.

In a another embodiment of the present invention, C9 carbon compounds are used in the process and are coupled with alkynes and propargyl compounds that can make valuable products for the chemical, pharmaceutical and oil industry. C9 compounds are used by the petroleum industry to make chemicals. The present invention provides a more environmentally friendly method because water is used in the solvent blend to couple C9 compounds with alkynes or propargyl alcohols.

In another embodiment of the present invention methyl and phenyl substituted indenes can be coupled with acetylenes and propargyl alcohols. Methyl and phenyl substituted indenes are not as reactive as aromatic compounds. In addition, methyl and phenyl substituted indenes are available from major chemical suppliers and are found in resin feeds to make other high value chemicals that are used by the plastics industry to make useful products. The process of the present invention provides a way to make other chemicals safely from indene chemicals because water is used and a micro flow reactor can be used to provide added advantages.

In another embodiment of the present invention, the process involves the use of batch chemical methods to make the indene coupled alkyne chemicals. Batch methods are very well known in the art and have been used for over 150 years and are accepted for use by one skilled in the art when synthesizing chemicals needed for several different applications and industries. Batch chemistry is used by countries with different economic capabilities and is used around the world to make chemicals on small scales and on industrial scales. The process of the present invention provides a method to make high value chemicals using batch methods.

Another embodiment of the process of the present invention involves pre-stirring the indene, alkyne and palladium salt blend for a period of time usually for at least 15-30 minutes. The pre-stirring of the chemicals increases mixing and provides a more efficient reaction and leads to less waste being made. The pre-stirring can be achieved using a batch flask with a stirrer or a micro flow reactor containing a mixing unit.

In another embodiment of the present invention, the process can use a micro flow reactor (Drawing 3) to obtain greater safety, better economic feasibility and reaction control when compared to batch methods. Other published methods have not disclosed the use of a microreactor to carry out the process outlined in the present invention which provides an advantage to the user from the benefits of increased reaction control, added safety and efficiency.

In another embodiment of the process of the present invention, a micro flow reactor can be used to increase reaction control of the chemical reaction. In addition, the micro flow reactor can provide more efficient mixing. The micro flow reactor has a mixing module to ensure a higher degree of blending and mixing when compared to other batch methods. This mixing module can ensure that a better mixing of the starting chemicals is obtained when compared to batch methods.

In another embodiment of the present invention, the process can be performed using a microreactor unit, tubing and HPLC pumps to pump the reaction fluid through the tubing and micro flow coil and microreactor chip. For example, a series of Gilson pumps can be used to pump a fluid containing the solvent blend, indene, base, and alkyne through the micro flow reactor disclosed in Drawing 3. The micro flow reactor provides control over reaction parameters such as temperature and time and can be monitored and controlled with a computer.

In another embodiment of the present invention, the micro flow reactor consists of a microreactor unit to provide variability in the microreactor chip that is used. The microreactor chip can be changed to have different engineering functionalities. In addition, the micro reactor chip can have different catalyst and chemicals coated on the inside of the channels and grooves. The microreactor chip and the micro flow coil unit has palladium coated on the inner channels and/or grooves that are used to contain the reaction fluid containing starting materials and products flowing through the channels and/or grooves. Some batch methods are not compatible in flow reactors due to precipitate formation. The process in the present invention does not form or use a precipitate.

In another embodiment of the process of the present invention, the micro flow reactor chip can be changed for an alternative chip with different engineering functionalities. This variability increases reaction design flexibility and optimization because different chips with different properties can be used. The micro flow reactor provides a way to rapidly vary conditions while monitoring the products that are made in a chemical process.

In another embodiment of the process of the present invention, the micro flow reactor can be controlled using a computer. The computer can provide automated control of temperature, pressure and flow rate. These reaction parameters are important when controlling a chemical reaction and are difficult to control with precision using batch methods. The automated control of these reaction parameters provides an opportunity to optimize reactions more rapidly than in batch methods in less time and with less waste formation.

In another embodiment of the present invention, the process has many advantages because copper is not required. The use of copper can produce unwanted homo coupled waste products by eliminating homo coupling of the acetylenes and alkynes. These homo coupled waste products are observed in other processes and lower efficiencies caused by unwanted waste. The formation of these wasteful chemicals can be difficult to control, especially in batch methods, and can be problematic to dispose in an environmentally sound way. The process of the present invention does not produce these homo coupled waste products.

In another embodiment of the present invention, the process provides a high degree of selectivity of the products that are formed. The high selectivity of the process provides several advantages over other processes that use alkynes because trimerized waste products are not formed. The products are not trimers of the alkynes, acetylenes or propargyl alcohols that are used in the process which can be problematic for other processes. One skilled in the art will appreciate that less waste is made in this process.

In another embodiment of the present invention, the micro flow reactor offers advantages over batch methods by not generating unwanted homo coupled waste products. The micro flow reactor provides increased reaction control when compared to batch methods and helps prevent the formation of homo coupled products. In some cases these undesirable can lower reaction efficiency. In addition, the homo-coupled products are not generated because copper is not used as an additive. Copper can catalyze the formation of homo-coupled products via Glässer couplings.

In another embodiment of the present invention, the process can use several different alkyne containing molecules. Both polar alkynes such as propargyl alcohol and non-polar alkynes such as phenyl acetylene can be used without any modifications. The process of the present invention allows coupling different types of alkynes containing polar and non-polar functionalities which can pose a challenge for other processes. Such challenges can be overcome by one skilled in the art when using the process described to couple indenes and alkynes.

In another embodiment of the present invention, alkyne trimerization is controlled which is problematic with all processes that use alkynes. The process of the present invention does not form trimerized products from alkynes which can be very problematic because of costs involved with inefficiencies resulting from the elimination of waste products. These unwanted trimerized waste products are not formed in the process of the present invention because of the higher selectivity that is achieved in the process.

In another embodiment of the present invention, a palladium salt blend is used which to provide the advantages of ease of handling and storage. In addition, the palladium salt blend can be used in catalytic or stoichiometric amounts. Other processes do not use palladium salt blends but instead use a catalyst which can be more costly and harder to store for long periods of time. The palladium salt blend that is used in the present invention can be blended in a customized way to contain other chemicals that may be needed for the process of the present invention.

In another embodiment of the present invention, the process involves pre stirring the indene and other starting materials for a period of time providing an increase in efficiency from increased blending and mixing of the starting materials. This will allow the process to work without additives. The use of additives can pose an environmental problem because of the disposal requirements of waste products made when using additives.

Yet another embodiment of the process of the present invention involves a more robust process because additives are not needed. Micellar forming chemicals are not needed which can be toxic and can be problematic when purifying final chemicals. The process of the present invention does not need micellar forming chemicals.

Another embodiment of the process of the present invention entails not needing copper co-catalysts or additives. Copper can be toxic and expensive and can be problematic because of the copper salts that can form during the reaction. The process of the present invention does not need copper catalysts. In addition, copper is expensive and can increase operating costs.

Another embodiment of the process of the present invention involves using an aerobic atmosphere. Some processes can't tolerate aerobic atmospheres due to decomposition problems of the chemicals that are used or the final chemical products that can be made. The process of the present invention provides advantages for one skilled in the art because the process can tolerate both aerobic and anaerobic atmospheres.

Another embodiment of the process of the present invention involves using an anaerobic atmosphere. Some processes can't tolerate anaerobic atmospheres due to decomposition problems of the chemicals that are used or the final chemical products that can be made. The process of the present invention provides advantages for one skilled in the art because the process can tolerate both aerobic and anaerobic atmospheres.

In another embodiment of the process of the present invention involves the use of different bases and solvent blends. Pyrrolidine and pyridine can be used as the bases in the process of the present invention. In addition, the bases can be used in a solvent blend with water to create a new solvent with different physical properties. In addition, pyridine and pyrrolidine can be used as solvents for the process if water is not available using a micro flow reactor.

In another embodiment of the process of the present invention a solvent blend can be used which can be a combination of two different solvents usually acetone, water, pyridine and pyrrolidine. This solvent blend provides an advantage to the user because the process can tolerate variability in the solvent properties. This can provide advantages in terms of economy from less waste being made.

Another embodiment of the process of the present invention involves the use of a detector in line with the micro flow reactor. The detector can be an infrared spectrometer and/or nuclear magnetic resonance instrument bearing a flow probe and/or a mass spectrometer to be used to detect the products and provide data in real time. This can increase efficiency from time savings by not having to wait as long for the results. This rapid data collection provides a more efficient way of obtaining the outcome of the chemical process described.

In yet another embodiment of the process of the present invention, the micro flow reactor disclosed has the reaction fluid passing inside the channels and/or grooves. The micro flow reactor provides advantages for one skilled in the art because the reaction fluid is contained within the closure of the channels and/or grooves. This provides control over reaction parameters in the flow of fluids that helps minimize the formation of unwanted hot spots that can lead to increased waste and lower selectivity and reaction efficiencies. In addition, this provides the advantage of added safety because a smaller volume of chemical is used which minimizes risks associated with using large amounts of chemicals.

In another embodiment of the process of the present invention, the micro flow reactor can regulate the temperature of the reaction fluid. The temperature enclosure described in the invention is capable of obtaining temperature ranges between −150 C to 350 C. This provides convenience for the user because an external heating apparatus is not required. This provides one skilled in the art to regulate the temperature with ease without the need for an external heating apparatus that has potential to lead to fires or explosion if exposed to flammable chemicals and solvents.

DRAWINGS

The embodiments of the present invention will now be described by reference using the drawings where reference numerals are used to describe the elements in the drawings.

Figure 1:
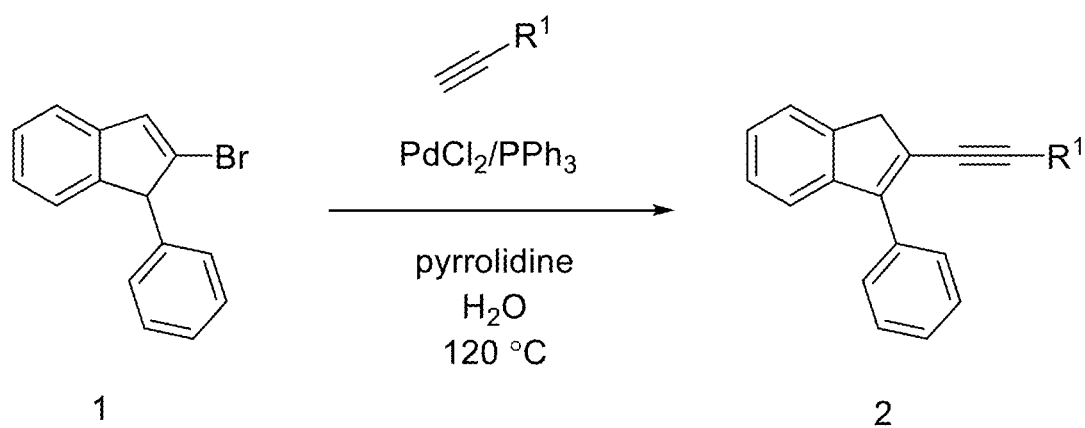
FIG. 1 shows the reaction scheme of the process in the present invention in which a 2-bromo-1-phenyl indene is coupled to an alkyne or a propargyl group to show a 2-alkynyl or 2-propargyl substituted indene.
Figure 2:
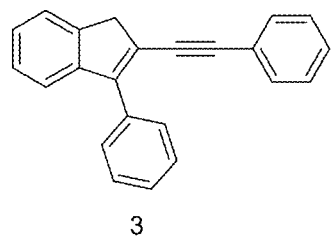
FIG. 2 shows the products of the process when phenyl acetylene or propargyl alcohol is combined with a 2-bromo-1-phenyl indene.
Figure 2:
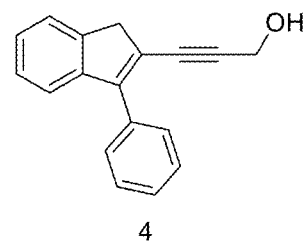
Figure 3:
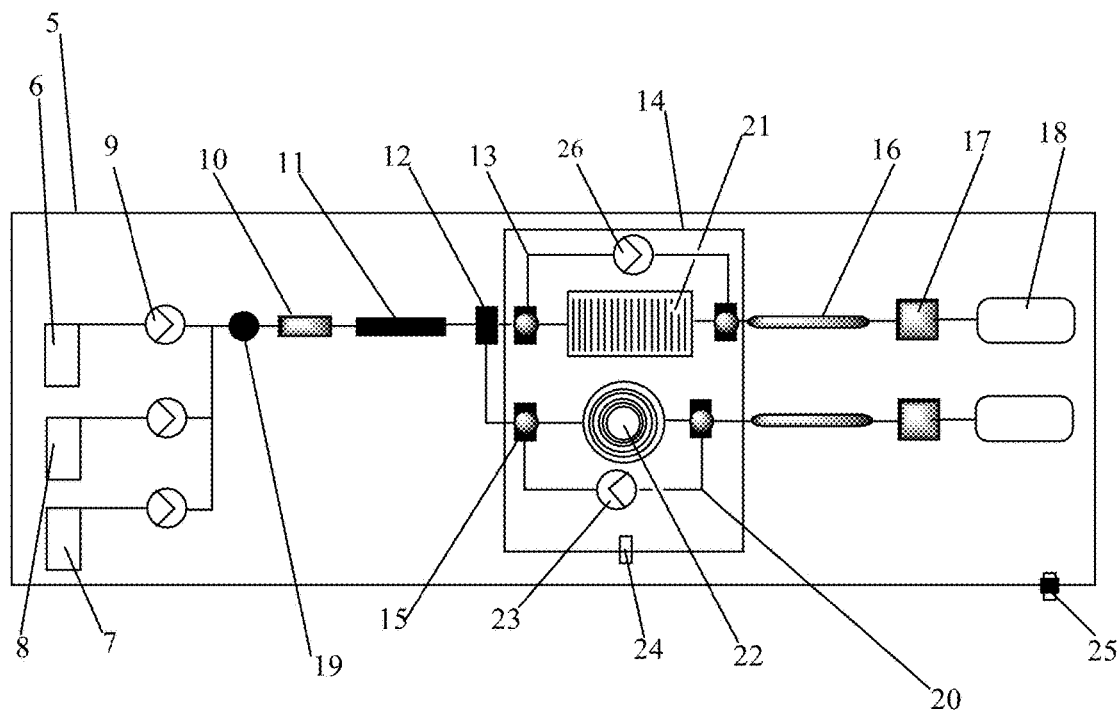
FIG. 3 shows the micro flow reactor.
Figure 4:
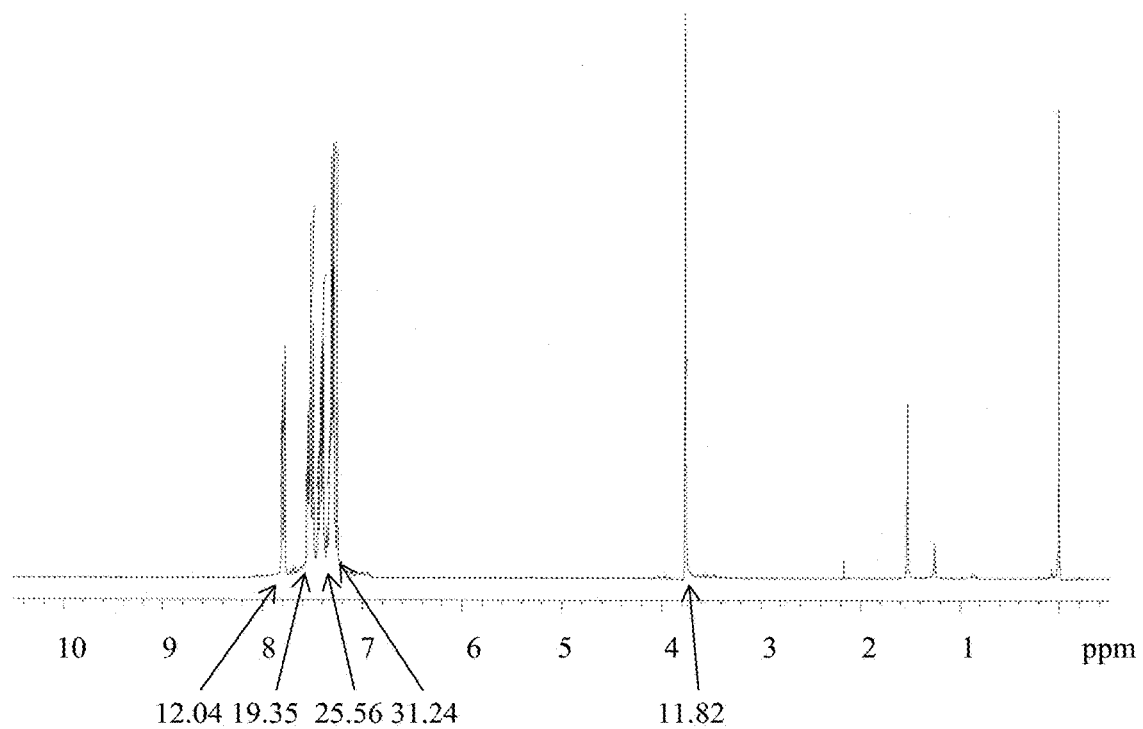
FIG. 4 shows a $^1$HNMR spectrum of the phenylacetylene derived product using the process in $CDCl_3$ with TMS.
Figure 5:
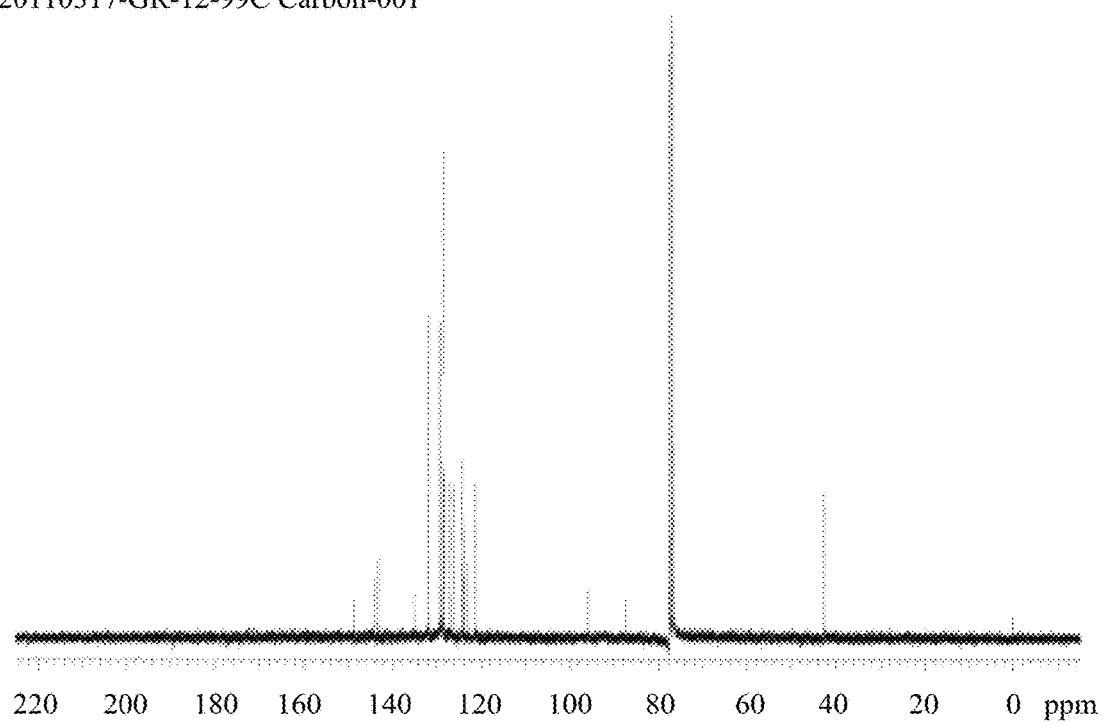
FIG. 5 shows a $^{13}$CNMR spectrum of the phenylacetylene derived product using the process in $CDCl_3$ with TMS.
Figure 6:
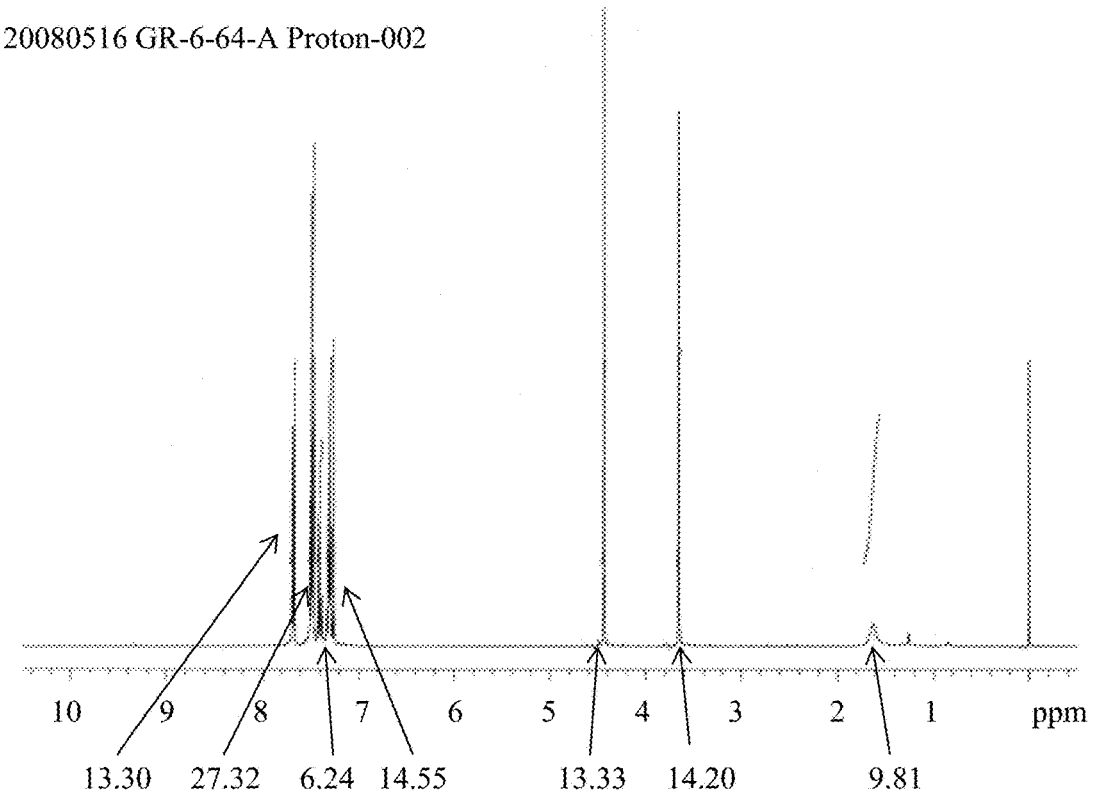
FIG. 6 shows a $^1$HNMR spectrum of the propargyl alcohol derived product using the process in $CDCl_3$ with TMS.
Figure 7:
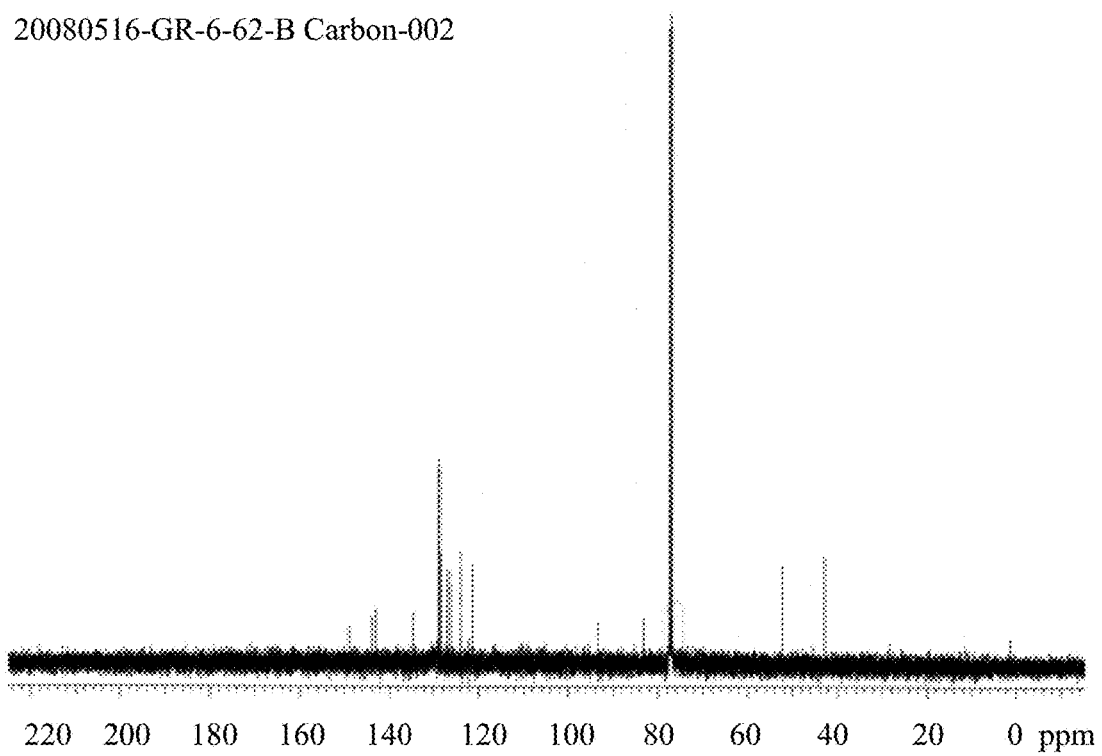
FIG. 7 shows a $^{13}$CNMR spectrum of the propargyl alcohol derived product using in $CDCl_3$ with TMS.

LEGEND FOR DRAWING REFERENCE LABELS 1 2-bromo-1-phenyl indene
2 2-alkynyl-1-phenyl indene
3 3-phenyl-2-(phenylethynyl)-1H-indene
4 3-(3-phenyl-1H-inden-2-yl)prop-2-yn-1-ol
5 Flow Reactor Closure to control anaerobic/aerobic atmosphere
6 Indene and alkyne storage inlet
7 Base storage inlet
8 Water storage inlet
9 Solvent/chemical pump
10 Mixing unit
11 Backpressure regulator
12 Switching valve
13 Microreactor reaction loop
14 Temperature regulating enclosure
15 Multi temperature valve
16 Base scavenging column
17 Detector
18 Chemical product collection containers
19 Inline filter
20 Micro channel disk reaction loop
21 Microreactor unit containing channels and grooves
22 Micro flow coil unit containing channels and grooves
23 Micro flow coil unit reaction loop pump
24 Aerobic/anaerobic atmosphere valve to temperature regulating enclosure
25 Aerobic/anaerobic atmosphere valve to micro flow reactor enclosure

The invention claimed is:

1. A chemical process comprising the steps of reacting a chemical reaction fluid comprising a base solvent blend comprising water, a palladium salt consisting essentially of palladium chloride, triphenylphosphine, an alkyne selected from one of phenylacetylene and propargyl alcohol which does not contain a pyridine group, and a substituted indene comprising 2-bromo-1-phenyl indene, in a vessel selected from one of a batch reactor and a-micro flow reactor that is sealed to form an alkyne coupled indene in an atmosphere selected from one of an aerobic atmosphere and an anaerobic atmosphere.

2. The chemical process of claim 1 wherein the reaction vessel is selected from one of a microreactor and a flow apparatus comprising pre-fabricated channels with dimensions of breadth and height ranging from 1 nanometer to 200 micrometers.

3. The chemical process of claim 2 wherein the reaction vessel is configured to pass the chemical reaction fluid inside the channels with distances travelled by the reaction fluid ranging from 1 mm to 1000 meters.

4. The chemical process of claim 2 wherein the reaction vessel is capable of temperature ranges from −150° C. to 350° C.

5. The chemical process of claim 2 wherein the reaction vessel is capable of altering and regulating the rate of reaction fluid flow and the residence times within the pre-fabricated channels.

6. The chemical process of claim 5 wherein the reaction fluid flow is within the range of 0.0001 mL/minute-500 L/min.

7. The chemical process of claim 5 wherein the reaction fluid flow residence times is within the ranges of 0.00001 seconds-100 hours.

8. The chemical process of claim 1 wherein a product of the process does not contain micelle forming compounds.

9. The chemical process of claim 1 wherein copper is not used as a co-catalyst in the vessel.

10. The chemical process according to claim 1, wherein a product of the process contains a molecule of the structure I, II, and IV or a molecule of structure 2:

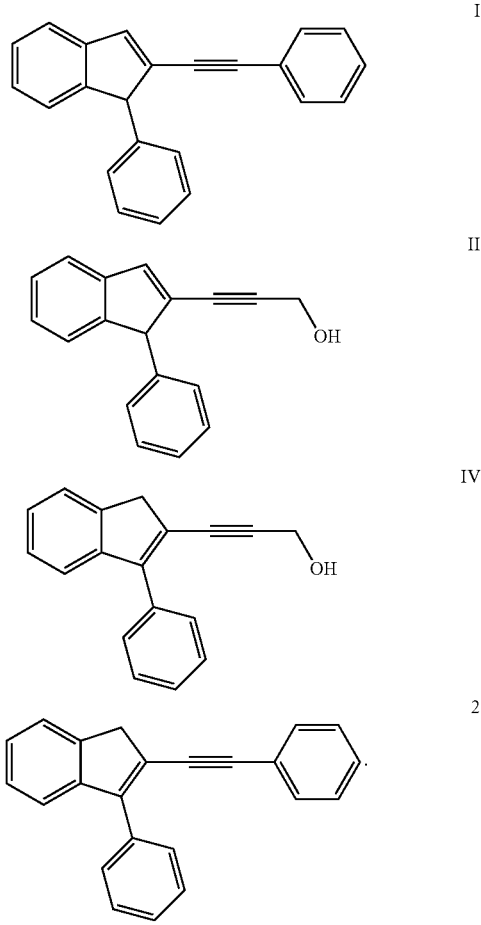

11. The chemical process of claim 1 comprising the steps of:
   a) Pre stirring the indene and the alkyne for a specified period of time;

b) Adding the palladium salt;
c) Adding the base solvent blend and a base; and
d) Heating the mixture for a specified period of time.

12. The chemical process of claim 11 wherein the base is selected from one of pyrrolidine and pyridine.

13. The chemical process of claim 11 wherein the base is pyrrolidine containing water in any amount.

14. The chemical process of claim 11 wherein the base is pyridine containing water in any amount.

15. The chemical process of claim 11 wherein the palladium salt comprises triphenylphosphine and an inert material.

16. The chemical process of claim 15 wherein the inert material does not affect the chemical process.

* * * * *